(12) United States Patent
Gao et al.

(10) Patent No.: US 10,017,800 B2
(45) Date of Patent: *Jul. 10, 2018

(54) CLEAN SUGAR AND LIGNIN FROM NON-CHEMICALLY PRETREATED LIGNOCELLULOSIC BIOMASS

(71) Applicant: INTERNATIONAL PAPER COMPANY, Memphis, TN (US)

(72) Inventors: Johnway Gao, Federal Way, WA (US); Amar N. Neogi, Kenmore, WA (US)

(73) Assignee: INTERNATIONAL PAPER COMPANY, Memphis, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/868,970

(22) Filed: Apr. 23, 2013

(65) Prior Publication Data

US 2014/0316162 A1    Oct. 23, 2014

(51) Int. Cl.
*C12P 19/00* (2006.01)
*C08B 1/00* (2006.01)
*C08L 97/00* (2006.01)
*C12P 19/02* (2006.01)

(52) U.S. Cl.
CPC ............... *C12P 19/00* (2013.01); *C08B 1/00* (2013.01); *C08L 97/005* (2013.01); *C12P 19/02* (2013.01)

(58) Field of Classification Search
CPC ........ C12P 19/00; C12P 19/02; C08L 97/005; C08B 1/00
USPC .............................. 127/30; 568/840; 562/589
See application file for complete search history.

(56) References Cited

U.S. PATENT DOCUMENTS

| | | | |
|---|---|---|---|
| 2,752,270 A * | 6/1956 | Specht | 127/37 |
| 2008/0227161 A1 | 9/2008 | Levie et al. | |
| 2010/0041119 A1 | 2/2010 | Christensen et al. | |
| 2011/0129889 A1 | 6/2011 | Inamdar et al. | |
| 2011/0250637 A1 | 10/2011 | Kurihara et al. | |
| 2012/0264873 A1 | 10/2012 | Eyal et al. | |

FOREIGN PATENT DOCUMENTS

WO    WO2010077170 A2    7/2010

OTHER PUBLICATIONS

Karunanithy et al. Influence of Extruder Temperature and Screw Speed on Pretreatment of Corn Stover while Varying Enzymes and Their Ratios. Appl Biochem Biotechnol 162:264-279, 2010.*
Claassen et al. Utilisation of biomass for the supply of energy carriers. Appl Microbiol Biotechnol 52: 741-755, 1999.*
Bashir et al. R etention of alkali, alkaline earth and transition metals on an itaconic acid cation-exchange column Eluent pH, ionic strength and temperature effects upon selectivity. Journal of Chromatography A, 964 (2002) 113-122.*
Zheng, et al., Overview of biomass pretreatment for cellulosic ethanol production, Int. J. Agric. & Biol. Eng., 2(3), pp. 51-68, 2009.
Agarwal, et al., Enzymatic hydrolysis of biomass: Effects of crystallinity, particle size, and lignin removal, Proceedings of the 16th ISWPFC, China Light Industry Press, 2011.
Taherzadeh, Muhammed, et al., Pretreatment of Lignocellulosic Wastes to Improve Ethanolo and Biogas Production: A Review. International Journal of Molecular Sciences, 2008, pp. 1621-1651.

* cited by examiner

*Primary Examiner* — Yih-Horng Shiao
(74) *Attorney, Agent, or Firm* — Christensen O'Connor Johnson Kindness PLLC

(57) ABSTRACT

Methods of producing clean (e.g., low sulfur and metal ion content, and free of fermentation inhibitors) sugar and lignin-rich streams, and downstream conversion products, from lignocellulosic biomass, may include obtaining non-chemically pretreated, milled lignocellulosic biomass, reacting the milled lignocellulosic biomass with an enzymatic agent to produce a slurry that includes converted monomeric lignocellulosic sugars and lignin-rich residuals, and separating the slurry into a sugar stream that includes the converted monomeric lignocellulosic sugars and a lignin-rich stream that includes the lignin-rich residuals. The sugar stream, not including water, includes at least 75% monomeric lignocellulosic sugar, less than 0.20% sulfur, and less than 3.0% metal ion content, and the lignin-rich stream includes at least 35% lignin and less than 0.50% sulfur. Some methods include producing fermentation products such as alcohols and/or organic acids from the sugar stream, and/or use of the lignin residuals in fuels.

18 Claims, 5 Drawing Sheets

CLEAN SUGAR AND LIGNIN FROM NON-CHEMICALLY PRETREATED LIGNOCELLULOSIC BIOMASS

TECHNICAL FIELD

This disclosure relates to enzymatic hydrolysis of lignocellulosic biomass, and in particular to the production of clean (e.g., having low sulfur and metal ion content, and being free of fermentation inhibitors and other impurities) sugar and lignin-rich streams, and downstream conversion products, from non-chemically pretreated, milled lignocellulosic biomass.

BACKGROUND

Lignocellulosic biomass represents an attractive and environmentally friendly starting material for production of carbohydrates (such as sugars) and downstream processes (such as fermentation to alcohols, organic acids, polymer precursors, etc.), and/or of lignin, since the raw material is obtained from renewable resources. Many non-food lignocellulosic materials are potential sources, including wood and by-products of wood processing (e.g., chips, sawdust, shavings).

Example methods of producing sugars from lignocellulosic biomass include acid hydrolysis and enzymatic hydrolysis. In acid hydrolysis, a mixture of woody material (such as wood chips) in acid is heated in the presence of water under conditions sufficient to hydrolyze cellulose, producing sugars and lignin residue. US20120264873 of Eyal, et al., discloses an example of a strong hydrochloric acid hydrolysis method. Acid is not consumed in the reaction, so the hydrolysis co-products typically include residual acid content. Additionally, in some acid hydrolysis methods, toxic degradation products are produced, including inhibitors of downstream fermentation (e.g., furans, such as hydroxymethylfurfural (HMF), furfuraldehyde, etc.). Removal of residual acid and inhibitors, such as by waching, ion exchanging, or other purification methods, represents additional cost and time.

Enzymatic hydrolysis proceeds by breaking cellulose chains into sugar molecules by suitable enzymes. The cellulose present in lignocellulosic biomass is recalcitrant to enzyme systems, largely due to the complex structure of plant cell walls, and generally requires pretreatment to make the cellulose fraction accessible by enzymatic hydrolysis. Chemical and organic solvent pretreatments are common, but such techniques are typically accompanied by significant cost, as well as a host of environmental management and waste treatment issues resulting from, or otherwise related to, use of the pretreatment chemicals. Example chemical pretreatment methods include sulfur dioxide treatment, oxidative delignification, ozonolysis, ammonia fiber explosion (AFEX), treatments with organosolvents and/or ionic liquids, and so forth (see, e.g., Zheng, et al., Overview of biomass pretreatment for cellulosic ethanol production, Int. J. Agric. & Biol. Eng., 2(3), pp 51-68, 2009). Besides material cost and regulatory requirements, like acid hydrolysis, chemical pretreatment methods characteristically introduce residual impurities into the hydrolysis reaction co-products. Moreover, many chemical pretreatment processes modify the lignin present in lignocellulosic biomass, and/or introduce impurities such as sulfur and sulfur compounds, which collectively create complexity and cost in isolation and/or use of such lignin, particularly in liquid fuel products for which low sulfur content is a requirement.

Example non-chemical pretreatment methods for enzymatic hydrolysis include steam explosion and liquid hot water pretreatment, both of which require significant energy costs. Moreover, even in these non-chemical methods, the use of hot water or steam have been known to result in acetic acid formation, which in turn reacts with hemicellulose sugar to form furfural during pretreatment (Harmsen et al., Literature review of physical and chemical pretreatment processes for lignocellulosic biomass, ECN-E-10-013, Energy Research Centre of the Netherlands, 2010).

Mechanical pretreatment, such as milling wood chips to fine wood powder to the extent that the tightly structured cell wall is opened, can increase susceptibility to enzymatic hydrolysis by allowing the enzymes to more readily contact the cellulose (see, e.g., Agarwal, et al., Enzymatic hydrolysis of biomass: Effects of crystallinity, particle size, and lignin removal, Proceedings of the $16^{th}$ ISWPFC, China Light Industry Press, 2011). However, typical milling techniques often require significant energy cost and/or time to yield a suitable particle size. Moreover, milling is often accompanied by one or more chemical processes, such as to remove pitch or lignin, to more efficiently achieve a desired particle size and/or powder consistency. In particular, delignification of milled biomass prior to enzymatic hydrolysis has been found to make the cellulose in milled biomass more accessible to the enzyme system used, such as by further increasing the surface area of the milled material by forming pores via lignin removal (Id.; see also WO2010077170 of Davidov et al.).

SUMMARY

The current disclosure describes methods of clean (e.g., free of fermentation inhibitors and other chemical residuals), low-sulfur lignocellulosic sugar and lignin-rich residual production from enzymatic hydrolysis performed on lignocellulosic biomass without chemical pretreatment, and products from such methods. Clean lignocellulosic hydrolysis products present fewer process and cost obstacles in various downstream applications, such as conversion of lignocellulosic sugar to alcohol, organic acids, polymer precursors, and so forth, and/or use of lignin-rich residuals.

An illustrative example method of lignocellulosic biomass conversion includes obtaining non-chemically pretreated, milled lignocellulosic biomass having a particle size of about 300 microns or less, reacting the milled biomass with an enzymatic agent (such as by means of enzymatic hydrolysis) to produce a slurry that includes converted monomeric lignocellulosic sugars and lignin-rich residuals, and separating the slurry into a sugar composition that includes the converted monomeric lignocellulosic sugars and a lignin-rich composition that includes the lignin-rich residuals. In contrast to methods incorporating chemical pretreatment, the slurry produced according to the methods of the present disclosure is free of furans and other fermentation inhibitors, as are the hydrolysis reaction co-products, i.e., the sugar composition and the lignin-rich composition. The sugar composition includes at least 75% monomeric lignocellulosic sugar and less than 0.20% sulfur, and less than 3.0% metal ion content after water is removed, and the lignin-rich composition includes at least 35% lignin and less than 0.5% sulfur.

In some methods, the biomass is milled, and/or otherwise processed prior to milled, such as by chipping, resizing, drying, etc., for example if the biomass is wood (such as softwood). Such processing steps will relate to the type of biomass used.

In some methods, separating the co-products is accomplished by means of filtering. In some methods, the slurry may additionally include undigested lignocellulosic biomass and/or unused enzymatic agent. In the latter case, some methods may include recycling the enzymatic agent, such as by adding fresh, or unreacted, lignocellulosic biomass to the slurry, for example to effect an additional hydrolysis reaction.

Some methods may further include drying or otherwise concentrating one or both of the sugar composition and the lignin-rich composition, such as by dewatering the sugar composition to produce a clean lignocellulosic sugar syrup, powder, or crystalline mixture, and/or drying the lignin-rich composition to achieve a solids content of a desired amount, such as 80% or above.

Some methods may further include downstream processing of the sugar composition and/or the lignin-rich composition, or concentrated versions thereof, such as by converting the lignocellulosic sugar composition to alcohol (or organic acid, or polymer precursor, etc.), suspending the lignin-rich composition in a fuel, and so forth.

Another illustrative example method of hydrolytic lignocellulosic biomass conversion in accordance with the present disclosure includes, in a first hydrolysis reaction, reacting milled lignocellulosic biomass with an enzymatic agent to produce a first slurry that includes converted lignocellulosic sugars, lignin-rich residuals, and unused enzymatic agent, then mixing additional milled lignocellulosic biomass with the first slurry to produce a slurry mixture, such as in a continuous mixing tube or tubular reactor outside the first hydrolysis reaction. The lignocellulosic sugars are then separated from the slurry mixture. In a second hydrolysis reaction, the milled lignocellulosic biomass in the slurry mixture is reacted with the enzymatic agent in the slurry mixture to produce a second slurry that includes converted lignocellulosic sugars and lignin-rich residuals. The converted lignocellulosic sugars are then separated from the second slurry. The separated sugars may then be combined, further filtered, and concentrated for downstream fermentation and/or other uses as indicated above.

Illustrative embodiments of a lignin-rich composition produced from lignocellulosic biomass according to the present disclosure include at least 40% lignin by weight and has an HHV of at least 9000 BTU/lb. Illustrative embodiments of sugar compositions produced from lignocellulosic biomass according to the present disclosure include at least 75% monomeric lignocellulosic sugar and have less than 0.20% sulfur content.

The concepts, features, methods, and component configurations briefly described above are clarified with reference to the accompanying drawings and detailed description below.

DETAILED DESCRIPTION

Lignocellulosic biomass represents an attractive and environmentally friendly starting material for production of carbohydrates (such as sugars) and downstream processes (such as fermentation to alcohols) since it is obtained from renewable resources. Many non-food lignocellulosic materials are potential sources, including wood (both hardwood and softwood), by-products of wood processing (e.g., chips, flakes, sawdust, shavings, and other wood residuals), as well as other agricultural residues, herbaceous energy crops, and so forth. In the illustrative embodiments and examples discussed herein, wood, and in particular softwood, is used as lignocellulosic biomass, in part due to low cost and high availability.

Compositions of various types of biomass vary, but generally include cellulose as the major component, followed by hemicellulose and lignin, and various proteins, oils, and ash.

Pretreatment, as the term is used in the context of enzymatic hydrolysis, refers to a process to prepare biomass to facilitate bioconversion, such as a process that converts biomass from its native form into a form suitable for cellulose hydrolysis. Several chemical pretreatments summarized above, while effective, result in chemical residue and/or lignin impurification in hydrolysis products, as well as require often significant material cost, and also represent health and environmental concerns.

Mechanical pretreatment of biomass, such as milling, especially to a particle size on the order of hundreds or even tens of microns, provides a material characterized by a vastly increased surface area and porosity (as compared with untreated biomass), and higher availability of the cellulose to enzymes. As noted above, some milling techniques commonly include solvent treatment steps, such as solvent extraction, to remove pitch, lignin, and/or other organic compounds prior to enzymatic hydrolysis. WO2010077170 of Davidov et al. provides such an example. However, the methods of the present disclosure employ no chemical pretreatment.

Figure 1:
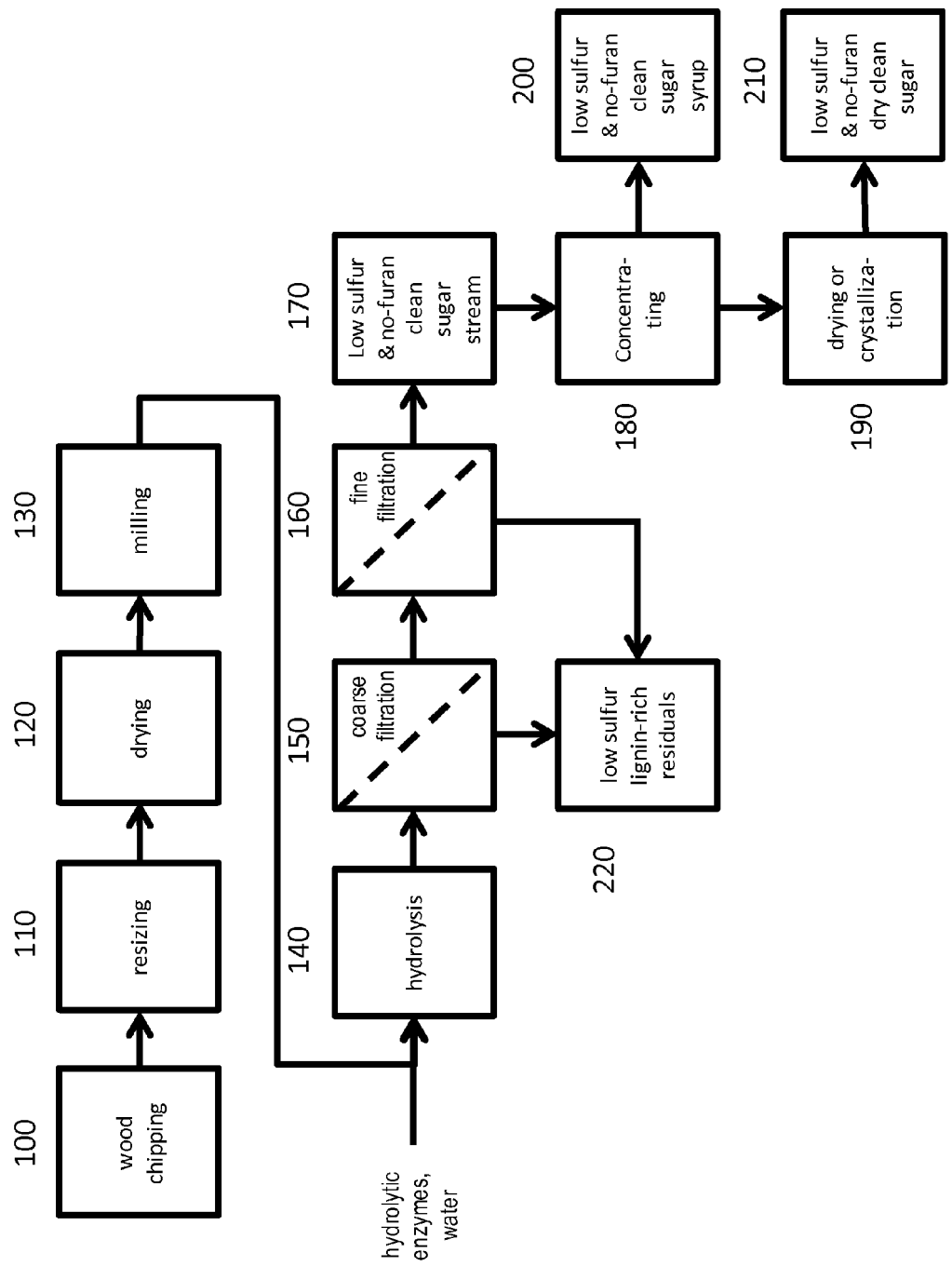
FIG. 1 is a flow chart schematically representing an illustrative example of a biomass conversion process in accordance with the present disclosure.
Figure 2:
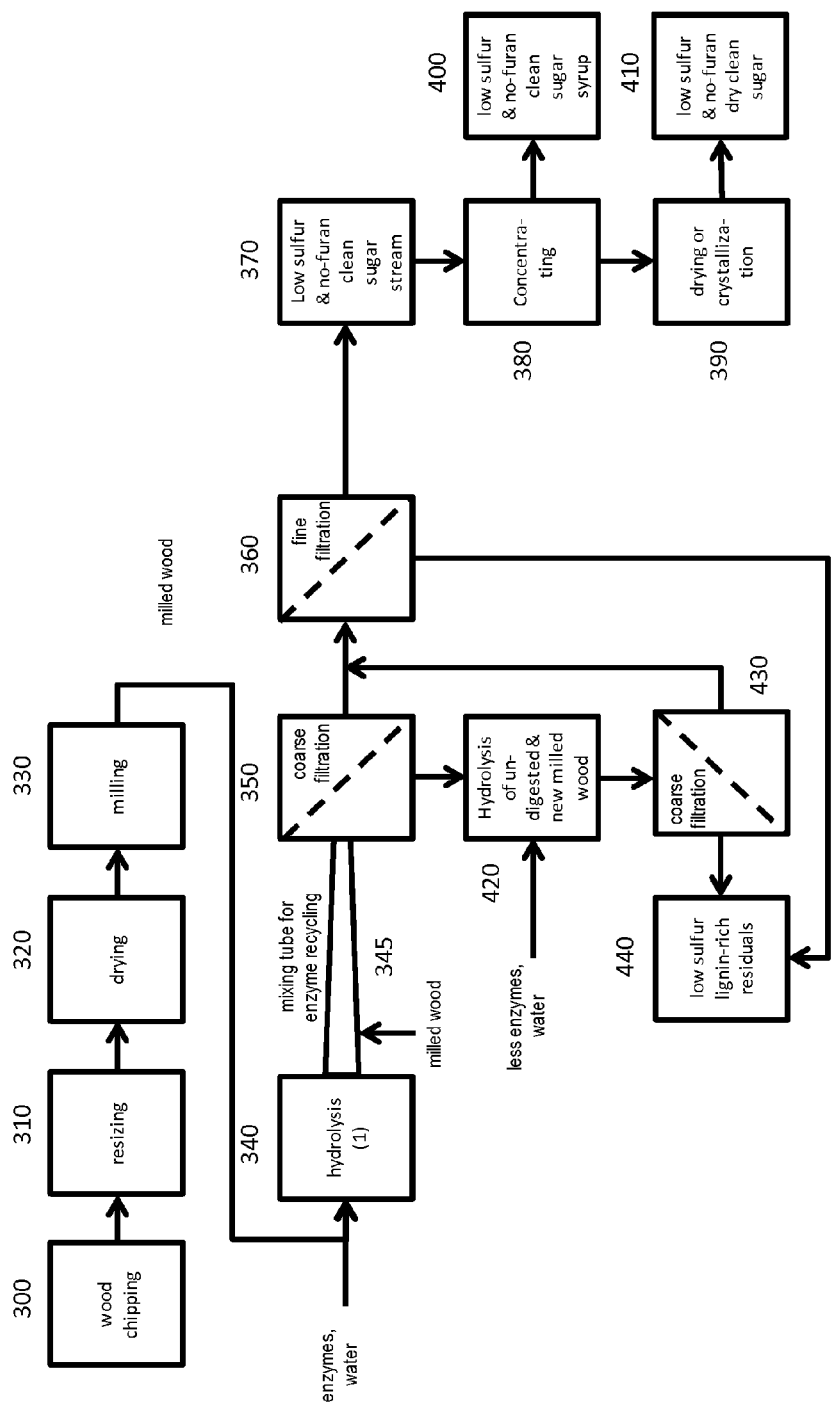
FIG. 2 is a flow chart schematically representing a further illustrative example of a biomass conversion process in accordance with the present disclosure.

Referring to the drawings, two illustrative and non-exclusive examples of biomass conversion processes are somewhat schematically indicated in FIGS. 1 and 2 to include a series of interconnected boxes that represent process steps. As will be evident from the description below, one or more of the represented process steps may further include multiple sub-steps or processes. As such, the represented steps are not exhaustive or exclusive of other steps and methods that may be consistent with those indicated in FIG. 1. Further, some methods may omit one or more of the represented steps, include steps not represented, combine steps, perform steps in a different order than as indicated, etc. The steps may be carried out in any suitable system or systems by one or more components, which may be co-located in the same facility or located in different facilities, and so forth.

In FIG. 1, the example biomass conversion process is shown to include preparation steps including wood chipping at 100, resizing at 110, drying at 120, and milling at 130. Such steps are optional to the methods disclosed herein, may vary depending on the nature of the biomass used, and may be performed according to suitable techniques. For example, milling is typically performed in one or more ball mills, such as in succession (e.g., coarse to fine), a tandem mill, and so forth. In the methods of the present disclosure, fine wood powder having a particle size of less than 300 microns (and in some cases less than 25 microns, or less than 10 microns) is obtained by use of a tandem mill and without chemical pretreatment. Optionally, the milling step may include screening, such as to isolate a desired particle size range.

Once non-chemically pretreated, milled lignocellulosic biomass having a preferred particle size is obtained, an enzymatic agent is allowed to react with the biomass under conditions suitable to effect cellulose hydrolysis, at 140. For example, the biomass sample is typically suspended in water, to which an aqueous solution of enzymatic agent is added, under suitable temperature and pH. Because fine biomass waters rapidly and tends to go down immediately (as compared with conventional wood chips, which float), water needs and hydrolysis preparation time can be minimized. The enzymatic agent, usually one or more enzymes or enzyme complexes of enzymes, such as cellulase enzymes and other enzymes useful in hydrolysis of polysaccharides (polymer sugars), is typically selected to match or otherwise target some or all of the polysaccharide components of the raw material. For example, in the examples discussed below, Douglas fir wood powder is used, and an enzymatic agent that includes enzyme complexes known to be suitable for conversion of lignocellulosic polysaccharides is used, e.g., CTec2 and HTec2 enzyme products available from Novozymes A/S, in appropriate ratios and under suitable temperature, pH, and other reaction conditions. Accordingly, the hydrolysis step may include temperature and/or pH control. For example, in the lab-scale experiments described below, a buffer (e.g., sodium citrate) is added to the hydrolysis solution and the pH is periodically adjusting (e.g., with NaOH). On an industrial scale, pH may be controlled by automated base or acid addition lines.

Hydrolysis produces a slurry consisting of a hydrolyzed product that includes converted monomeric lignocellulosic sugars, as well as lignin-rich residuals, and which may also include undigested raw materials (e.g., milled biomass) and/or unused enzymatic agent. The slurry is clean, that is, the slurry is free of furans and other fermentation inhibitors, and extremely low in sulfur content, as a result of the non-chemical pretreatment of the raw materials. At 150 and 160, the slurry is separated into a clean sugar composition (which includes the converted monomeric lignocellulosic sugars) and a clean lignin-rich composition (which includes the lignin-rich residuals and other components, if any). In the example process, the separation is accomplished by means of filtration, and in particular a coarse filtration at 150, followed by a fine filtration at 160, in which the sugar composition is the filtrate. The filtrate contains water, converted monomeric lignocellulosic sugars, and other components including some amount of water soluble wood extractives, and a small amount of insolubles, such as undigested hemicellulose, cellulose, lignin and wood extractives, which in total are about 3-7% (or less) of the total monomeric sugar content. However, in methods consistent with the present disclosure, separation may be achieved by any suitable method, which may or may not include one or more filtration steps.

The sugar composition, or clean sugar stream, generated at 170 from the slurry, is aqueous, and is typically characterized by a monomeric lignocellulosic sugar titer of about 8-10% (wt/vol), a sulfur content less than about 0.02% (wt/wt), a metal content less than about 0.5% (wt/wt), and no furan content. Not including the water content, the sugar composition of the clean sugar stream ranges from about 85-95% (wt/wt), with the sulfur content less than 0.20% (wt/wt), and with soluble wood extractives and insoluble organic compounds such as undigested cellulose, hemicelluloses, lignin, wood extractives, and so forth, accounting for about 3-7% (wt/wt).

Optionally, a concentrating step (at 180), and/or a drying or crystallization step (at 190) may be employed to produce a clean sugar syrup (at 200) or a clean dry sugar mixture (at 210), such as by any suitable technique(s).

The solid stream produced, at 220, from the filtration (at 150 and 160) includes the lignin-rich composition, in which the sulfur content is less than 0.1% by weight. Although not shown, the lignin-rich composition may be subjected to further processing, such as washing (to remove unreacted biomass and/or enzymes), dewatering (to increase solids content), and so forth.

A second illustrative and non-exclusive example of a biomass conversion process is somewhat schematically indicated in FIG. 2. The process in FIG. 2 includes many of the same process steps as described above, but incorporates modifications that integrate biomass residual and enzyme recycling into the process. To the extent that various steps represented in FIG. 2 are similar to those described above with respect to FIG. 1, they are summarized in the paragraphs below.

Milled lignocellulosic biomass such as wood powder may be prepared in a series of preparation steps, for example wood chipping (at 300), chip resizing (at 310), chip drying (at 320) and milling (at 330), in which the wood is milled into wood powder. As noted above, the preparation of the biomass is shown not to include any chemical pretreatment. Once obtained, the milled biomass is hydrolyzed in a first hydrolysis reaction, at 340, by hydrolytic enzymes to produce a slurry that includes monomeric lignocellulosic sugars (i.e., glucose, xylose, mannose, arabinose and galactose), while no fermentation inhibitors are formed, e.g. furans such as hydroxymethylfurfural and furfuraldehyde.

The slurry is transported from the first hydrolysis reaction 340, which may take place in a suitable reaction tank or vessel ("hydrolysis unit"), to a filtration unit or suitable separation process, such as by means of a mixing tube 345 or appropriate conduit. A new milled biomass stream is continuously added to the mixing tube 345 to mix with the slurry transported from the first hydrolysis reaction, such as by means of a static mixer or otherwise. As such, the mixing tube allows mixing of the enzyme in the slurry and the binding of the unused enzymes to the new milled wood. This "slurry mixture," which includes the undigested wood residuals and the new milled wood bound with enzyme, is transported to a separation process, shown as two separate filtration units 350 and 360, although a different separation process configuration may be used. In filtration unit 350, a course filtration process separates the solid of the undigested wood residuals and the new milled wood bound with enzymes away from the liquid stream containing monomeric sugars. In a second hydrolysis reaction conducted at 420, less enzymatic agent is needed per unit of undigested raw material due to the enzyme recycling step in 345 and 350. The second hydrolysis reaction 420 produces a second slurry, which is sent to another course filtration unit 430, which separates out the low sulfur lignin-rich residuals, at 440. The filtrate from course filtration unit 430 is transported to fine filtration unit 360 for a fine filtration, to produce a low sulfur and no-furan clean lignocellulosic sugar stream, indicated at 370. After 370, a concentrating step (at 380) may produce a low sulfur and no-furan clean lignocellulosic sugar syrup, at 400. Further, an optional drying step (at 390) may produce a low sulfur and no-furan lignocellulosic dry sugar product, at 410.

Although not shown in the drawings, methods according to the present disclosure may optionally include any of several downstream processes performed on the clean sugar and/or lignin products prepared as above. For example, the clean sugar stream and/or concentrated products thereof (syrups, dry mixtures, and so forth) may be converted to alcohols or other products by suitable fermentation techniques. Accordingly, methods may include producing alcohol from the converted monomeric lignocellulosic sugars in the sugar composition. However, because there is no furan inhibitor present in the clean sugar stream, there is no need to remove inhibitor prior to fermentation, such as would be the case with standard chemical pretreatment methods including acid hydrolysis. Fermentation methods in accordance with the present disclosure may include, as a preliminary step, clarification of the sugar composition (or a concentrated version thereof), such as by filtering, centrifuging, etc., followed by inoculation with an appropriate fermentation agent, such as a yeast strain chosen to use one or more of the sugars present in the sugar composition for fermentation. For example, C6 sugars such as glucose and mannose may readily be converted to ethanol using various baker's yeast strains. Accordingly, target fermentation alcohol products may also include isobutanol, and so forth. Reaction conditions such as temperature, pH, time, and so forth, would be as suitable for the target fermentation alcohol product(s) according to standard methods.

Another example of a product that may be produced from the clean sugar stream and/or concentrated products is lactic acid. Accordingly, methods that include producing lactic acid from the converted monomeric lignocellulosic sugars in the sugar composition may include clarification of the sugar composition followed by addition of an appropriate fermentation agent and, if appropriate, other reagents suitable to create a fermenting medium. An example fermentation agent for lactic acid formation is *Lactobacillus rhamnosus*, which may be inoculated in a fermentation medium in the presence of the clean sugar stream under suitable conditions to effect lactic acid fermentation.

Conversion of sugars to other downstream products, including other organic acids, polymer precursors, and so forth, are known in the art, and methods according to the present disclosure may include additional steps directed to producing such products from the sugar compositions produced herein. The absence of inhibitors and impurities in the sugar compositions provides several process advantages in such conversion processes, such as by not requiring interim purification steps.

As another example, the lignin-rich residuals may be dewatered and/or subjected to additional steps to purify the lignin. After the enzymatic hydrolysis and the filtration process as described in FIGS. 1 and 2, a lignin-rich residual stream is produced. This lignin-rich stream normally has a moisture content of about 70-90% (or a solid content ranging from 10-30%). This high moisture stream may be dewatered, such as by pressing or screw-pressing, to a much higher solid content, such as 40-60%. After the pressing step, the lignin-rich stream is further dried in dryer, e.g. a rotary drum dryer, or other drying devices. Once the lignin is dried to about or higher than 80% solids, this lignin-rich stream can be pelletized in a pelletizer to make a solid fuel. This solid fuel can be used and burnt for energy generation and/or steam generation in a co-firing boiler with biomass, a biomass boiler, a drying kiln, and a household wood stove, so forth.

The physical form of the dried lignin may be as suitable for the application. For example, the dried lignin-rich residuals may milled to very fine particles, such as 5-25 microns. The milled and fine lignin-rich powder can then be used and sprayed as a powder fuel as a combustion fuel in a co-firing boiler with biomass, a biomass boiler, a drying kiln, and so forth. Since the lignin-rich particles are very fine, the micron size lignin-rich particles can be used as an additive in a liquid fuel, such as a biodiesel, a diesel, and an alcohol.

The following examples summarize representative experiments of converting non-chemically pretreated milled lignocellulosic biomass in accordance with the methods and concepts discussed above.

Example 1. Douglas Fir Wood Chip Preparation and Composition

The softwood wood chips used in this example are Douglas fir wood chips (debarked) from the Weyerhaeuser Longview Pulp Mill in Washington, U.S. The wood chips were first dried to contain less than 10% moisture. The carbohydrate composition of Douglas fir chips was determined by converting the polymeric sugars in the wood chips into monomeric sugars such as glucose, xylose, mannose, arabinose and galactose. Table 1 shows the original polymeric sugar composition of the Douglas fir wood chips. The total polymeric sugar composition for the debarked Douglas fir chip sample is 59.07% (wt/wt). The lignin content of the Douglas fir sample is 27.10% (wt/wt).

TABLE 1

Douglas fir chip carbohydrate composition

| Polymer sugar | Composition (% wt/wt) |
|---|---|
| Arabinan | 1.01 |
| Galactan | 2.53 |
| Glucan | 38.87 |
| Xylan | 3.90 |
| Mannan | 11.77 |
| Total | 59.07 |

Example 2. Douglas-Fir Wood Chip Milling and Milled Wood Powder Composition

The Douglas fir chips were milled down to wood powder in a tandem mill by the Kenko Corporation, Tokyo. The carbohydrate composition of the milled Douglas fir wood powder is shown in Table 2. The total polymeric sugar composition for the milled Douglas fir wood powder is 61.00% (wt/wt).

TABLE 2

Milled Douglas fir powder carbohydrate composition

| Polymer sugar | Composition (% wt/wt) |
|---|---|
| Arabinan | 1.00 |
| Galactan | 2.66 |
| Glucan | 41.20 |

TABLE 2-continued

Milled Douglas fir powder carbohydrate composition

| Polymer sugar | Composition (% wt/wt) |
|---|---|
| Xylan | 3.74 |
| Mannan | 12.40 |
| Total | 61.00 |

The milled Douglas fir wood powder was diluted in deionized water with sonication to break apart the aggregated particles. Two samples were plated on glass slides. After drying, each sample slide was imagined under scanning electron microscope. The particle sizes of two samples were analyzed, and the distributions were found to include about 95-99% of the particles having a size (diameter) smaller than about 25 microns. About 87-93% of the particles of the two samples had a size (diameter) less than about 10 microns. All of the particles in the two samples were under 300 microns in size.

Example 3. Clean Sugar Stream Production from Douglas Fir Wood Powder Hydrolysis The milled Douglas fir wood powder from Example 2 was hydrolyzed at 20% consistency with 4.7% (wt/wt) of CTec2 enzyme product (a cellulase enzyme) along with 0.4% (wt/wt) of HTec2 enzyme product (a xylanase enzyme), both from Novozymes A/S of Bagsvaerd, Denmark. The hydrolysis tests were conducted in 150 ml volume in 250 ml Erlenmeyer shake flasks. The hydrolysis pH (4.8-5.3) of the milled wood slurry was buffered by a 100 mmol sodium citrate buffer with periodic pH adjustment with a NaOH solution. The hydrolysis temperature was controlled at 50° C. and agitation was done by shaking the flask at 200 rpm in an orbital environmental shaking incubator.

Figure 3:
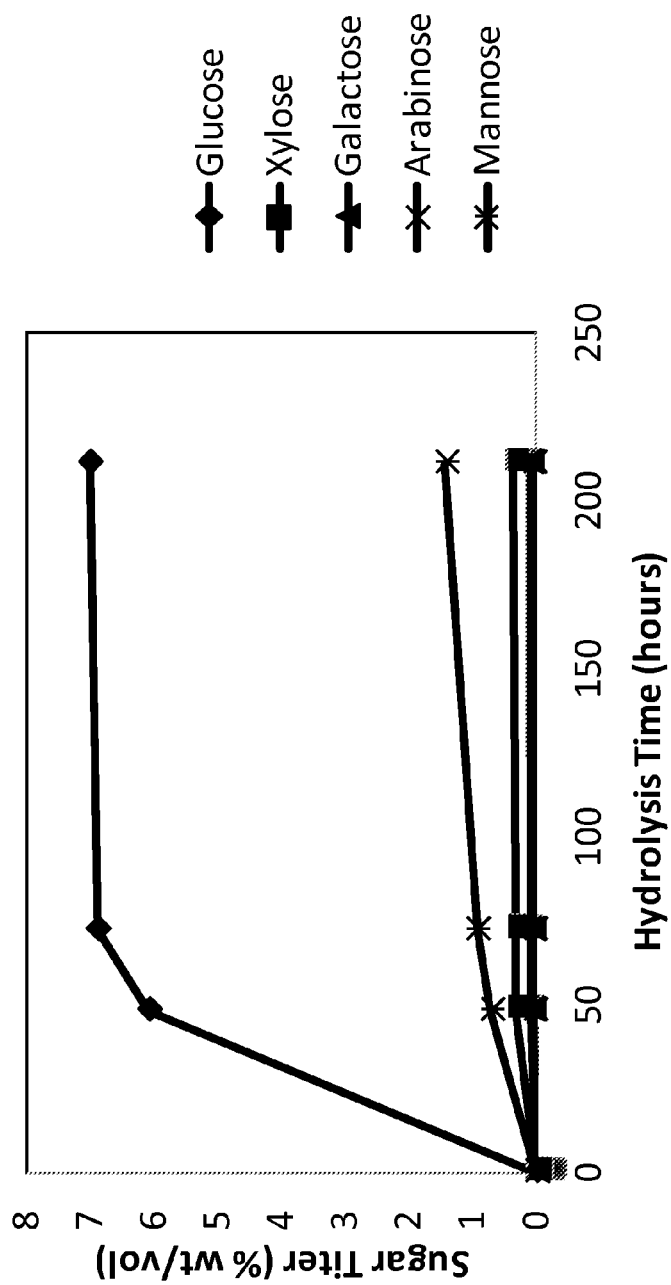
FIG. 3 is a graph showing monomeric sugar profiles of an example sugar stream prepared by performing enzymatic hydrolysis on a milled Douglas fir wood sample in accordance with the present disclosure.

After the slurry hydrolysis, the watery slurry mainly consists of monomeric lignocellulosic sugars and undigested residuals containing hemicellulose, cellulose and wood lignin. The monomeric sugar profiles of the milled Douglas fir wood (at a consistency of 20%) hydrolysis is shown in FIG. 3. The hydrolysis of the milled Douglas fir wood leveled off after three days of hydrolysis to achieve a total sugar titer of 8.2%. The total sugar titer at the end of the hydrolysis was 8.9% (wt/vol) after about 9 days of hydrolysis. Table 3 shows the monomeric sugar titers of each sugar in the end of the hydrolysis.

TABLE 3

Monomeric sugar titers in hydrolyzed Douglas fir wood powder (20% consistency)

| Monomeric sugar | Titer (% wt/vol) |
|---|---|
| Arabinose | 0.03 |
| Galactose | 0.09 |
| Glucose | 7.01 |
| Xylose | 0.36 |
| Mannose | 1.41 |
| Total | 8.90 |

No fermentation inhibitors such as hydroxymethylfurfural and furfural were found in the hydrolysis, as shown in Table 4.

TABLE 4

Furan titers in hydrolyzed Douglas fir wood powder (20% consistency)

| Furan | Titer (% wt/vol) |
|---|---|
| Hydroxymethylfurfural | 0.000 |
| Furfural | 0.000 |
| Total | 0.000 |

The sulfur content of the hydrolyzed Douglas fir wood powder slurry was analyzed, and the result is shown in Table 5. The wood milling process is a non-chemical and non-sulfite pretreatment method, and therefore, the sulfur content is extremely low. Without being bound by theory, the sulfur content is thought be carried from the original wood composition. The sulfur titer in the filtrate of the hydrolyzed milled wood is 0.016% (wt/wt). Samples 1 and 2 are from different milled Douglas fir samples.

TABLE 5

Sulfur content of filtrate of hydrolyzed milled Douglas fir wood powder

| Sample | Sulfur Titer (% wt/wt) |
|---|---|
| 1 | 0.016 |
| 2 | 0.016 |

The hydrolysis residuals from the above hydrolysis of the milled Douglas fir wood powder were analyzed for the lignin content, higher heating value and sulfur content. Douglas fir wood has a lignin content of about 27.10% (wt/wt). Table 6 shows that the hydrolysis residuals of milled Douglas fir wood have higher lignin content compared to the original Douglas fir wood chips, as well as high BTU HHV values and low sulfur.

TABLE 6

Characteristics of residuals from milled Douglas fir wood powder hydrolysis

| Sample | Lignin (% wt/wt) | HHV (BTU/lb residuals) | Sulfur (% wt/wt) |
|---|---|---|---|
| 1 | 45.6 | 9060 | 0.068 |
| 2 | 54.3 | 9596 | 0.055 |

The clean sugar stream was analyzed for metal and inorganic elements, and the results are shown in Table 7 below. The major metal and some inorganic element content in the clean sugar stream was 0.50% (wt/wt) and 0.39% (wt/wt), respectively, for clean sugar stream sample 1 and sample 2. The sodium citrate buffer contributed significant sodium content to the samples (a debarked softwood chip normally only has sodium content around 50 mg/kg wood). Besides the sodium from the sodium citrate buffer, sodium hydroxide used for pH adjustment contributed to sodium level of 0.1% to 0.2% of the total element level in the clean sugar stream.

TABLE 7

Element titer in clean sugar stream samples from hydrolyzed Douglas fir wood powder

| Sample Element | 1 (mg/kg clean sugar stream) | 2 (mg/kg clean sugar stream) |
|---|---|---|
| Ag | — | — |
| Al | 6.3 | 3.4 |
| As | — | — |
| B | 0.5 | 0.4 |
| Ba | 1.3 | 1.0 |
| Be | — | — |
| Bi | — | — |
| Ca | 142.1 | 91.3 |
| Cd | — | — |
| Co | — | — |
| Cr | 0.2 | 0.2 |
| Cu | 2.2 | 1.1 |
| Fe | 149.4 | 156.6 |
| K | 310.3 | 224.5 |
| Li | — | — |
| Mg | 13.5 | 9.9 |
| Mn | 5.2 | 4.3 |
| Mo | 0.0 | 0.0 |
| Na | 4,307.9 | 3,380.3 |
| Ni | 0.1 | 0.1 |
| P | 17.3 | 13.5 |
| Pb | 0.0 | — |
| Sb | — | — |
| Se | — | — |
| Sn | — | — |
| Sr | 0.5 | 0.4 |
| Tl | — | — |
| V | — | — |
| Zn | 5.8 | 2.9 |
| Total Element Content | 4,962.7 0.50% (wt/wt) | 3,890.0 0.39% (wt/wt) |

Note:
"-" indicates content (if any) is below detection limit at analysis.

When water is evaporated from the clean sugar stream, concentrated clean sugar streams are produced. Titers of lignocellulosic sugar monomers, metals and inorganic elements, and sulfur content of example concentrates are shown in Table 8. The total titer is less than 100%, which is balanced with water and other components (including some amount of water soluble wood extractives, and some small amount of insolubles, such as undigested hemicellulose, cellulose, lignin and wood extractives, which in total are about or less than 3-7% of the total monomeric sugar content). The sugar composition (water not included) in the clean stream ranges from 86.8 to 90.9%. Fine filtration may be used to remove such components. Although not tested, it can be calculated that if about 50% of such components are removed by a fine filtration, the sugar composition (water not included) in the clean stream will increase to 89.5 to 92.2%.

TABLE 8

Sugar titer and composition in clean sugar stream and concentrates

| Items | Concentrating factor Original Titer | 2.81 Product 1 | 5.62 Product 2 | 9.66 Product 3 |
|---|---|---|---|---|
| Sugar titer (%) | 8.90 | 25.00 | 50.00 | 86.00 |
| Major metal and inorganic (%) | 0.16-0.27 | 0.45-0.76 | 0.90-1.52 | 1.55-2.61 |
| Sulfur (%) | 0.016 | 0.045 | 0.090 | 0.153 |
| Other components (%) | 0.27-0.62 | 0.75-1.75 | 1.50-3.50 | 2.58-6.02 |
| Sugar Composition (%), water not included | 86.8-90.9 | | | |

Example 4. Clean Sugar Stream Fermentation to Ethanol

A clean sugar stream from the above hydrolyzed wood slurry in Example 3 was prepared by a clarification in a centrifuge to remove the coarse residuals and a filtration through a 0.45 micron filter to remove the finer particles large than 0.45 micron. The 0.45 micron filtration also served as a means to sterilize the sugar stream for the subsequent fermentation tests. The clean sugar stream is transparent and has a light amber color, showing no apparent particulates. The clean sugar stream was concentrated in a vacuum evaporator to form a high sugar titer syrup in order to achieve a high ethanol titer.

Figure 4:
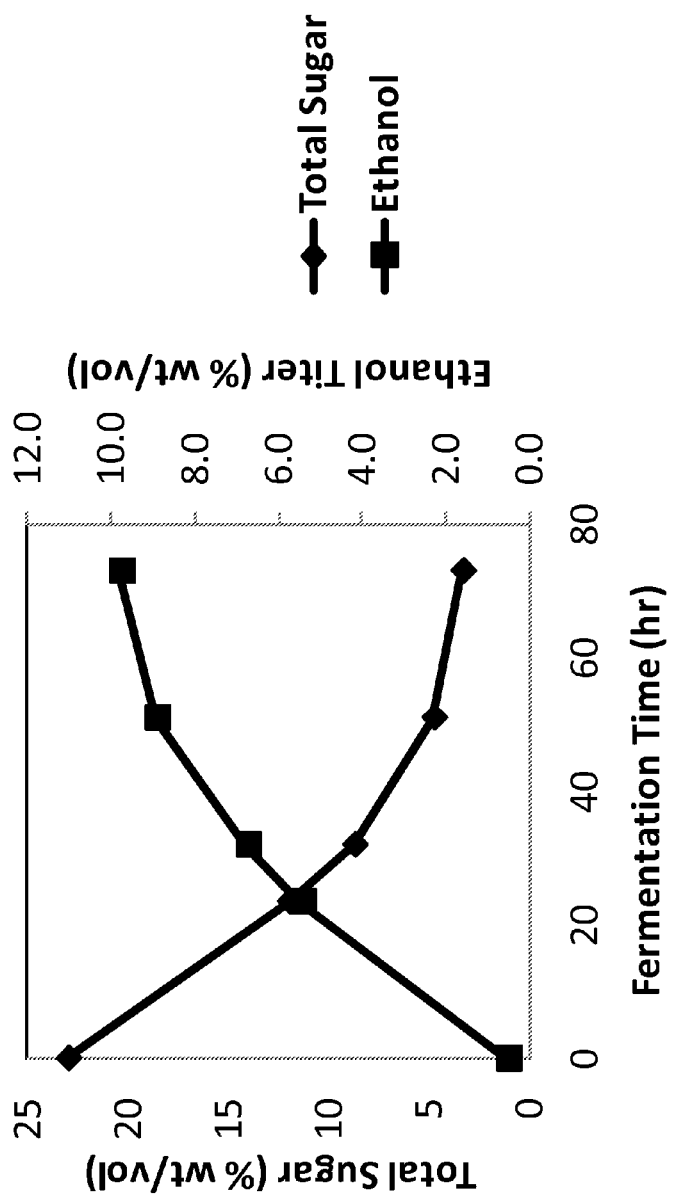
FIG. 4 is a graph showing the total ethanol titer and the total sugar consumption during ethanol fermentation of the example sugar stream shown in FIG. 3.

The ethanol fermentation medium was made from the clean sugar stream syrup supplemented with 0.5% corn steep liquor and 0.07% urea. The initial total sugar titer was 23.1% (wt/vol). An overnight grown baker's yeast strain NABC XR was inoculated at 2 g/L in the ethanol fermentation medium in a 50 ml shake flask. This yeast strain uses C6 sugar for ethanol fermentation, i.e., glucose and mannose were used, but not xylose and arabinose. The fermentation was conducted in an orbital shaking incubator at 33° C. and 100 rpm. The initial fermentation pH was 5.0. During fermentation, the pH was checked twice daily and readjusted back to pH 4.5-5.0 with a 20% KOH solution. FIG. 4 shows the total ethanol titer and the total sugar consumption during the ethanol fermentation. At the end of the 3-day fermentation, an ethanol titer of 9.8% (wt/vol) was achieved.

Example 5. Clean Sugar Stream Fermentation to Lactic Acid

The clean sugar stream from Example 4, without further sugar concentrating, was used as the carbon source for lactic acid fermentation. A lactic acid fermenting bacteria strain, *Lactobacillus rhamnosus* ATCC11443, was obtained from American Type Culture Collection (ATCC). The fermentation medium contains the clean sugar stream supplemented with nutrients 0.87 g/L peptone, 0.43 g/L yeast extract, 0.004 g/L $MnSO_4 \cdot H_2O$, 0.17 g/L $NaH_2PO_4$, 0.36 g/L $MgCl_2 \cdot 6H_2O$ and 0.17 g/L $(NH_4)_2SO_4$. The fermentation medium had an initial pH of 6.5. The medium was filter-sterilized through a 0.45 micron filter cup. Culture tubes (20 ml size) and rubber septa were sterilized at 250° F. for 15 minutes before lactic acid fermentation. A seed culture medium with all the nutrients and 4% glucose was used to propagate the *Lactobacillus rhamnosus* strain. The lactic acid fermentation was conducted in a total volume of 11.5 ml in 20 ml anaerobic culture tubes. After the medium was dispensed to each tube, the tube was sealed with rubber septa with a crimper. The headspace of each tube was purged with 5% hydrogen and 5% carbon dioxide balanced with nitrogen.

The *Lactobacillus rhamnosus* seed culture was grown for 24 hours in the same nutrient medium with 4% glucose. The ready *Lactobacillus* seed was centrifuged down and re-suspended in 1 ml nutrient medium without sugar and used as the seed culture. The fermentation medium was inoculated with 0.5 ml seed culture. The fermentation was conducted in an incubator at 37° C. The fermentation pH was checked daily and readjusted to pH 5.0-6.0 with a NaOH solution.

Figure 5:
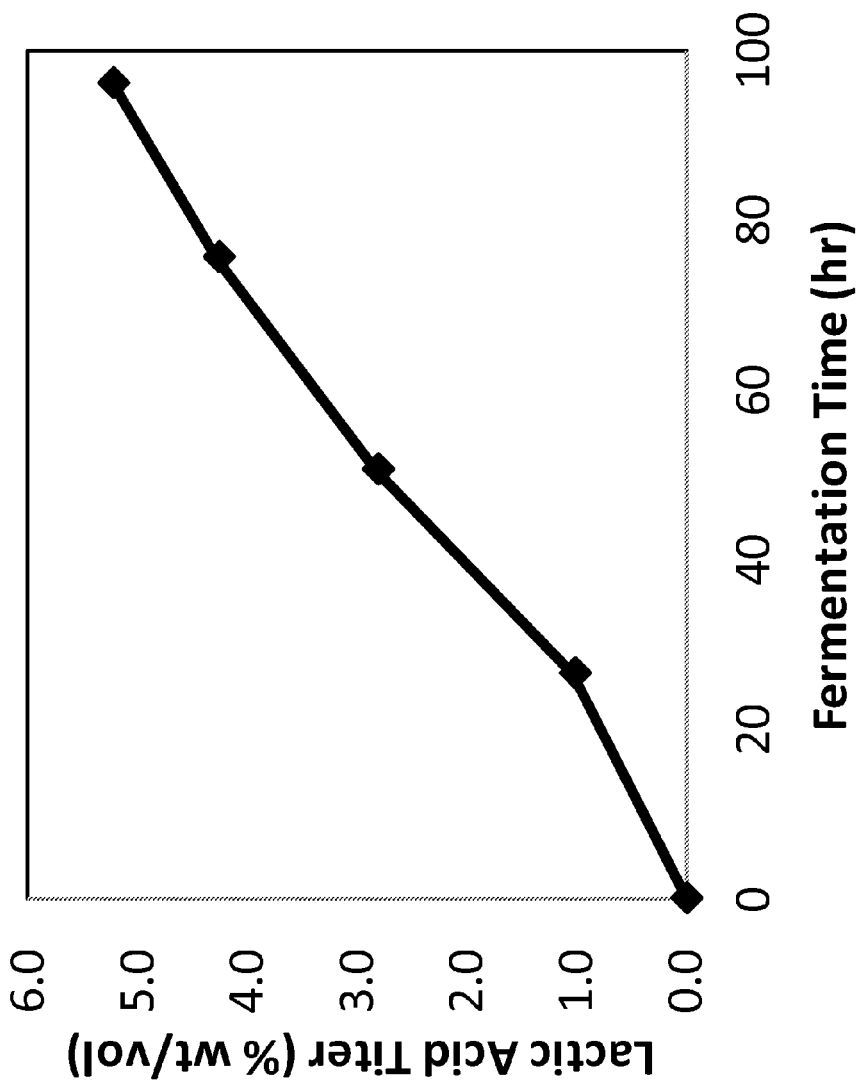
FIG. 5 is a graph showing lactic acid accumulation in a lactic acid fermentation process performed on the example sugar stream shown in FIG. 3.

The *Lactobacillus rhamnosus* was very active in lactic acid fermentation. The fermentation dropped quickly to less than pH 4.5 daily and was readjusted back to pH 5.0 to 6.0 daily. FIG. 5 shows the lactic acid accumulation in the fermentation. At the end of day 4, the lactic acid achieved 5.2% (wt/vol). This test showed that the clean sugar stream from milled Douglas fir wood supported well the bacterial lactic acid fermentation by *Lactobacillus rhamnosus*.

Example 6. Suspension of Lignin-Rich Residuals Particles in a Liquid Fuel

To test suitability for incorporation of the lignin-rich residuals in a liquid fuel, the lignin-rich residuals from Example 3 was dried and milled with a mortar and pestle to form a fine powder, having a particle size of about 5-25 microns. Various amount of the lignin residual powder were mixed with canola oil. The lignin residual particles were well-suspended in the oil without a quick settling down. The various suspensions of lignin in the oil and the calculated HHV of the oil and lignin mixture are shown in Table 9.

TABLE 9

Calculated HHV for suspensions of lignin-rich residuals in oil

| Lignin residual in oil (% wt/wt) | Calculated HHV (BTU/lb) |
|---|---|
| 53.3 | 12,550 |
| 33.3 | 13,857 |
| 20.0 | 14,729 |
| 14.3 | 15,102 |
| 10.5 | 15,348 |
| 6.8 | 15,589 |
| 0.0 | 16,000 |

Depending on BTU value needs, the lignin-rich residuals may be blended with a liquid fuel and the resulting lignin-rich residual and oil mixture still have high HHV value, and may be suitable for use as liquid fuel.

Illustrative, non-exclusive examples of descriptions of some methods and compositions in accordance with the scope of the present disclosure are presented in the following numbered paragraphs. The following paragraphs are not intended to be an exhaustive set of descriptions, and are not intended to define minimum or maximum scopes, or required elements or steps, of the present disclosure. Rather, they are provided as illustrative examples of selected methods and compositions that are within the scope of the present disclosure, with other descriptions of broader or narrower scopes, or combinations thereof, not specifically listed herein still being within the scope of the present disclosure.

A. A method of lignocellulosic biomass conversion, the method comprising:

obtaining non-chemically pretreated, milled lignocellulosic biomass having a particle size less than about 300 microns;

reacting the milled lignocellulosic biomass with an enzymatic agent to produce a slurry that includes converted monomeric lignocellulosic sugars and lignin-rich residuals; and separating the slurry into a sugar composition that includes the converted monomeric lignocellulosic sugars and a lignin-rich composition that includes the lignin-rich residuals;

wherein the sugar composition, not including water, includes at least 75% monomeric lignocellulosic sugar, less than 0.20% sulfur, and less than 3.0% metal ion content; and wherein the lignin-rich composition includes at least 35% lignin and less than 0.50% sulfur.

A.1. The method of paragraph A, wherein obtaining milled lignocellulosic biomass includes milling lignocellulosic biomass.

A.1.1. The method of paragraph A or A.1, further including one or more of chipping, resizing, and drying lignocellulosic biomass, prior to milling.

A.2 The method of any of paragraphs A through A.1.1, wherein the lignocellulosic biomass is wood.

A.2.1. The method of any of paragraphs A through A.2, wherein the wood is softwood.

A.3 The method of any of paragraphs A through A.2.1, wherein the milled lignocellulosic biomass has a particle size less than about 25 microns.

A.3.1 The method of any of paragraphs A through A.3, wherein the milled lignocellulosic biomass has a particle size less than about 10 microns.

A.4 The method of any of paragraphs A through A.3.1, wherein the slurry is free of furans and other fermentation inhibitors.

A.5 The method of any of paragraphs A through A.4, wherein separating the slurry includes filtering the slurry to yield a filtrate that includes the sugar composition, and a high solid stream that includes the lignin-rich composition and undigested lignocellulosic biomass.

A.6 The method of any of paragraphs A through A.5, further comprising, subsequent to separating the slurry, dewatering the sugar composition to produce a concentrated lignocellulosic sugar mixture.

A.6.1 The concentrated lignocellulosic sugar mixture produced according to the method of paragraph A.6.

A.6.2. A dry lignocellulosic sugar mixture produced according to the method of paragraph A.6.

A.7 The method of any of paragraphs A through A.6.1, further comprising, subsequent to separating the slurry, drying the lignin-rich composition to produce a lignin composition having a solid content of at least 80%.

A.7.1 The lignin composition produced according to the method of paragraph A.7.

A.8 The method of any of paragraphs A through A.7.1, wherein reacting the milled lignocellulosic biomass with an enzymatic agent includes recycling the enzymatic agent.

A.8.1. The method of paragraph A.8, wherein the slurry includes unused enzymatic agent; and wherein recycling the enzymatic agent includes adding fresh, unreacted milled lignocellulosic biomass to the slurry.

A.8.1.1. The method of paragraph A.8.1, wherein adding milled lignocellulosic biomass to the slurry is performed prior to separating the slurry.

A.8.1.2. The method of paragraph A.8.1, wherein separating the hydrolysis product mixture includes filtering the converted monomeric lignocellulosic sugars from the slurry to leave the lignin-rich residuals, undigested lignicellulosic biomass, and unused enzymatic agent.

A.9 The method of any of paragraphs A through A.8.1.2, wherein the composition of the sugar composition, not including water, includes at least 85.0% (w/w) monomeric lignocellulosic sugar.

A.9.1 The method of any of paragraphs A through A.9, wherein the composition of the sugar composition, not including water, includes at least 90.0% (w/w) monomeric lignocellulosic sugar.

A.10. The method of any of paragraphs A through A.9.1, wherein the composition of the sugar composition, including water, has a sugar titer of at least 8.9% (wt/vol).

A.11 The method of any of paragraphs A through A.10, wherein the composition of the sugar composition, including water, has a metal ion content of less than about 0.50% (wt/wt).

A.12 The method of any of paragraphs A through A.11, wherein the composition of the sugar composition, including water, has a sulfur content of less than about 0.02% (wt/wt).

A.13 The sugar composition produced by the method of any of paragraphs A through A.12.

A.14 The lignin-rich composition produced by the method of any of paragraphs A through A.12.

A.15 The method of any of paragraphs A through A.14, further comprising producing an alcohol fermentation product from the converted monomeric lignocellulosic sugars in the sugar composition.

A.15.1 The method of paragraph A.15, wherein the alcohol fermentation product includes ethanol.

A.15.2. The method of paragraph A.15, wherein the alcohol fermentation product includes isobutanol.

A.15.2. The alcohol produced by the method of any of paragraphs A.15 through A.15.2.

A.16 The method of any of paragraphs A through A.15, further comprising producing an organic acid fermentation product from the converted monomeric lignocellulosic sugars in the sugar composition.

A.16.1 The method of paragraph A.16, wherein the organic acid fermentation product includes lactic acid.

A.16 The method of any of paragraphs A through A.14, further comprising producing lactic acid from the converted monomeric lignocellulosic sugars in the sugar composition.

B.1 A method of hydrolytic lignocellulosic biomass conversion, the method comprising:
in a first hydrolysis reaction, reacting non-chemically pretreated, milled lignocellulosic biomass to with an enzymatic agent to produce a first slurry that includes converted lignocellulosic sugars, lignin-rich residuals, and unused enzymatic agent;
mixing additional non-chemically pretreated, milled lignocellulosic biomass with the first slurry to produce a slurry mixture;
separating the converted lignocellulosic sugars from the slurry mixture;
in a second hydrolysis reaction, reacting the milled lignocellulosic biomass in the slurry mixture with the unused enzymatic agent in the slurry mixture to produce a second slurry that includes converted lignocellulosic sugars and lignin-rich residuals; and
separating the converted lignocellulosic sugars from the second slurry.

B.1 The method of paragraph B,
wherein the first hydrolysis reaction is carried out in a hydrolysis unit;
wherein the separating is carried out in a filtration unit; and
wherein the mixing is carried out while transporting the slurry mixture from the hydrolysis unit to the filtration unit.

B.1.1 The method of paragraph B or B.1, wherein the mixing is performed continuously.

B.2. The method of any of paragraphs B through B.1.1, further including combining the converted lignocellulosic sugars separated from the first and second slurries.

B.3 The method of any of paragraphs B through B.2, further including adding additional enzymatic agent to the second hydrolysis reaction.

B.4 The method of any of paragraphs B through B.3, further including combining the lignin-rich residuals from the first and second slurries.

C.1 A lignin-rich composition produced from lignocellulosic biomass, the lignin-rich composition comprising at least 40% lignin by weight and having an HHV of at least 9000 BTU/lb.

C.1 The lignin-rich composition of paragraph C, wherein the sulfur content is less than 0.1% by weight.

C.2 The lignin-rich composition of paragraph C or C.1, comprising at least 45% lignin by weight.

C.3 The lignin-rich composition of any of paragraphs C through C.2, comprising at least 50% lignin by weight.

C.4 The lignin-rich composition of any of paragraphs C through C.3, comprising at least 54% lignin by weight.

C.5 The lignin-rich composition of any of paragraphs C through C.4, having an HHV of at least 9500 BTU/lb.

C.6 A liquid fuel mixture including the lignin-rich composition of any of paragraphs C through C.5.

C.6.1 The liquid fuel mixture of paragraph C.6, wherein the liquid fuel is one or more of a diesel fuel, a biodiesel fuel, and an ethanol fuel.

C.6.2 The liquid fuel mixture of paragraph C.6 or C.6.1, containing 5-80% of the lignin-rich composition.

C.6.3 The liquid fuel mixture of any of paragraphs C.6 through C.6.2, wherein the lignin-rich composition has a particle sizes of 5-30 microns.

C.6.4 The liquid fuel mixture of any of paragraphs C.6 through C.6.2, wherein the lignin-rich composition has a particle sizes of 10-15 microns.

C.7 The use of the lignin-rich composition of any of paragraphs C through C.5 as a solid fuel.

C.8 Any of the lignin-rich compositions of any of paragraphs C through C.5 produced by the method of any of paragraphs A through B.4.

D. A lignocellulosic sugar composition produced from lignocellulosic biomass, the sugar composition, not including water, comprising at least 75% monomeric lignocellulosic sugar and having a sulfur content less than about 0.20%.

D.1. The lignocellulosic sugar composition of paragraph D, wherein the sugar composition, not including water, comprises at least 85% monomeric lignocellulosic sugar.

D.2 The lignocellulosic sugar composition of paragraph D or D.1, wherein the sugar composition, not including water, comprises at least 90% monomeric lignocellulosic sugar.

D.3 The lignocellulosic sugar composition of any of paragraphs D through D.2, wherein the sugar composition, not including water, includes less than 3.0% metal ion content.

D.4 The lignocellulosic sugar composition of any of paragraphs D through D.3, wherein the sugar composition is aqueous, and has a sugar titer of at least 8.9% (wt/vol).

D.4.1 The lignocellulosic sugar composition of paragraph D.4, wherein the aqueous sugar composition has a sulfur content of less than about 0.02% (wt/wt).

D.4.2 The lignocellulosic sugar composition of paragraph D.4 or D.4.1, wherein the aqueous sugar composition has a metal ion content of less than about 0.50% (wt/wt).

D.5 Any of the lignocellulosic sugar compositions of any of paragraphs D through D.4.2 produced by the method of any of paragraphs A through B.4.

The disclosures of the references cited herein are incorporated by reference in their entireties.

Although the present invention has been shown and described with reference to the foregoing operational principles and illustrated examples and embodiments, it will be apparent to those skilled in the art that various changes in form and detail may be made without departing from the spirit and scope of the invention. The present invention is intended to embrace all such alternatives, modifications and variances that fall within the scope of the appended claims.

What is claimed is:

1. A lignocellulosic sugar composition from a softwood lignocellulosic biomass, wherein the lignocellulosic sugar composition, not including water, comprises at least 75% (wt/wt) monomeric lignocellulosic sugar, has a sulfur content less than about 0.20% (wt/wt), has a metal ion content of at least 0.45% (wt/wt) and less than 3.0% (wt/wt), and has a ratio of monomeric glucose plus monomeric mannose to at least one other monomeric lignocellulosic sugar greater than or equal to 93.6 and less than or equal to 280.7, wherein the at least one other monomeric lignocellulosic sugar is selected from the group consisting of galactose and arabinose.

2. The lignocellulosic sugar composition of claim 1, wherein the softwood lignocellulosic biomass is Douglas fir.

3. The lignocellulosic sugar composition of claim 2, wherein the lignocellulosic sugar composition, not including water, comprises at least 85% (wt/wt) monomeric lignocellulosic sugar.

4. The lignocellulosic sugar composition of claim 2, wherein the lignocellulosic sugar composition, not including water, comprises at least 90% (wt/wt) monomeric lignocellulosic sugar.

5. The lignocellulosic sugar composition of claim 2, wherein the lignocellulosic sugar composition is aqueous, and has a sugar titer of at least 8.9% (wt/vol).

6. The aqueous lignocellulosic sugar composition of claim 5, wherein the aqueous lignocellulosic sugar composition has a sulfur content of less than about 0.02% (wt/wt).

7. The aqueous lignocellulosic sugar composition of claim 5, wherein the aqueous lignocellulosic sugar composition has a metal ion content of less than about 0.5% (wt/wt).

8. The lignocellulosic sugar composition of claim 2, wherein the lignocellulosic sugar composition is free of furan and other fermentation inhibitors.

9. The lignocellulosic sugar composition of claim 2, wherein the lignocellulosic biomass from which the lignocellulosic sugar composition is produced is non-chemically pretreated.

10. The lignocellulosic sugar composition of claim 9, wherein the composition is produced by enzymatic hydrolysis of the non-chemically pretreated lignocellulosic biomass.

11. The lignocellulosic sugar composition of claim 2, wherein the Douglas Fir is debarked.

12. A lignocellulosic sugar composition from a softwood lignocellulosic biomass, wherein the lignocellulosic sugar composition, not including water, comprises at least 75% (wt/wt) monomeric lignocellulosic sugar, has a sulfur content less than about 0.20% (wt/wt), has a metal ion content of at least 0.45% (wt/wt) and less than 3.0% (wt/wt), and has a ratio of monomeric glucose to at least one other monomeric lignocellulosic sugar greater than or equal to 77.9 and less than or equal to 233.7, wherein the at least one other monomeric lignocellulosic sugar is selected from the group consisting of arabinose and galactose.

13. The lignocellulosic sugar composition of claim 12, wherein the softwood lignocellulosic biomass is Douglas fir.

14. The lignocellulosic sugar composition of claim 13, wherein the Douglas Fir is debarked.

15. The lignocellulosic sugar composition of claim 14, wherein the lignocellulosic sugar composition, not including water, comprises at least 85% (wt/wt) monomeric lignocellulosic sugar.

16. The lignocellulosic sugar composition of claim 14, wherein the lignocellulosic sugar composition is aqueous with a sugar titer of at least 8.9% (wt/vol) and has a sulfur content of less than about 0.02% (wt/wt).

17. The lignocellulosic sugar composition of claim 14, wherein the lignocellulosic sugar composition is aqueous with a sugar titer of at least 8.9% (wt/vol) and has a metal ion content of less than about 0.5% (wt/wt).

18. The lignocellulosic sugar composition of claim 14, wherein the lignocellulosic sugar composition is aqueous with a sugar titer of at least 8.9% (wt/vol) and is free of furan and other fermentation inhibitors.

\* \* \* \* \*